United States Patent [19]

Robinson

[11] Patent Number: 5,027,809
[45] Date of Patent: Jul. 2, 1991

[54] "PEEPER" PERFORMANCE HAND HELD NEBULIZER ATTACHMENT WITH ADJUSTABILITY OF EXPIRATORY PRESSURES AND EXPIRATORY RESTRICTION

[76] Inventor: Pat D. Robinson, 20865 Palamino Rd., Pine Grove, Calif. 95665

[21] Appl. No.: 524,786

[22] Filed: May 17, 1990

[51] Int. Cl.5 ............................................. A61M 16/08
[52] U.S. Cl. .......................... 128/203.24; 128/204.18; 128/200.14; 128/200.29; 128/203.12; 128/203.25; 128/204.26; 128/911; 128/912
[58] Field of Search .................................. 285/903, 14; 128/200.14, 202.22, 203.12, 203.23, 203.25, 200.23, 200.24, 911, 912; 128/200.21, 204.18, 204.26, 203.24

[56] References Cited

U.S. PATENT DOCUMENTS

| | | | |
|---|---|---|---|
| 3,664,337 | 5/1972 | Lindsey et al. | 128/200.21 X |
| 3,762,409 | 10/1973 | Lester | 128/200.14 |
| 3,826,255 | 7/1974 | Havstad et al. | 128/200.18 |
| 4,253,468 | 3/1981 | Lehmbeck | 128/726 |
| 4,446,863 | 5/1984 | Rubin et al. | 128/204.18 |
| 4,512,341 | 4/1985 | Lester | 128/200.21 |

FOREIGN PATENT DOCUMENTS 8601731  3/1986  World Int. Prop. O. ...... 128/200.21

Primary Examiner—Edgar S. Burr
Assistant Examiner—Eric P. Raciti

[57] ABSTRACT

An attachment for a prior art, hand-held, aerosol generating nebulizer, which enables the patient by flexing a flexible hose containing adjustable exhalation holes to control range of passive to active exhalation resistance, and which also contains a one-way valve to prevent medication wastage, and yet, allow the patient to draw in room air as needed. Also, included is a circular or wide oval shaped mouthpiece that allows the patient to inhale freely without the restriction of the conventional flat mouthpiece.

14 Claims, 3 Drawing Sheets

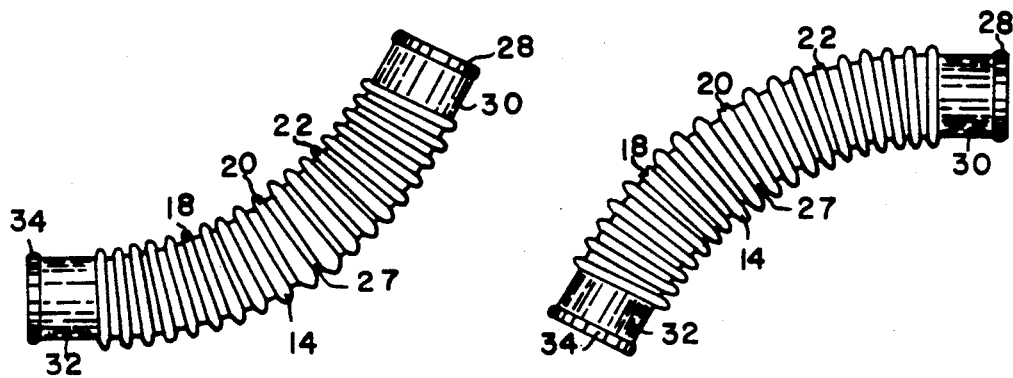
FIG 3-A  FIG 3-B
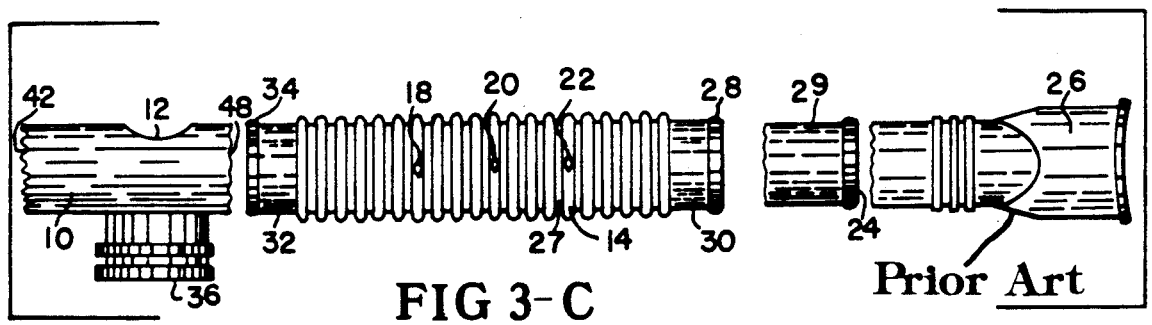
FIG 3-C  Prior Art
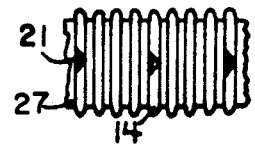
FIG 3-D
FIG 3-E
FIG 3-F

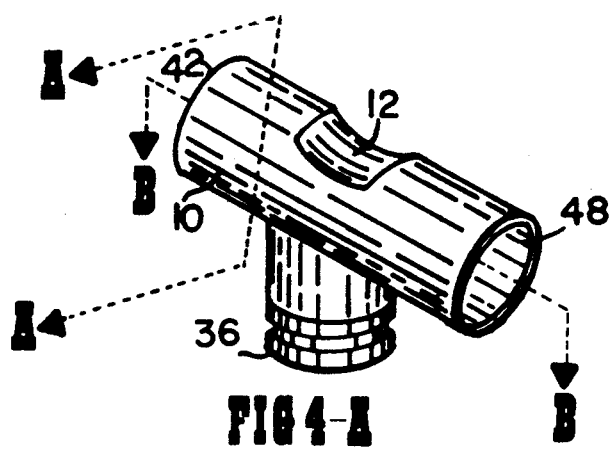
FIG 4-A
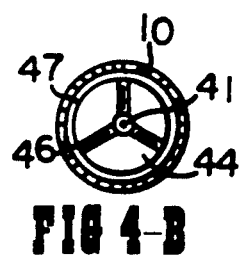
FIG 4-B
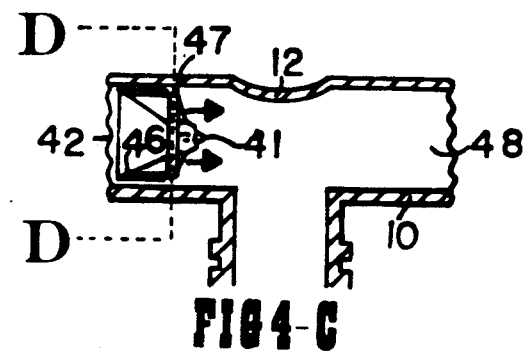
FIG 4-C
FIG 6
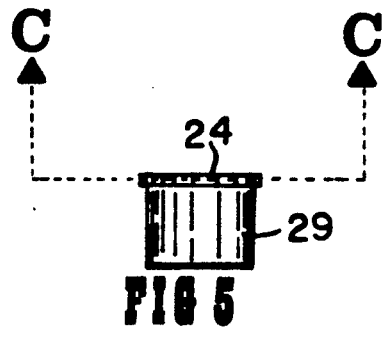
FIG 5
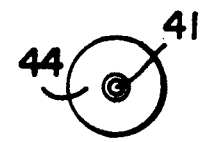
FIG 7
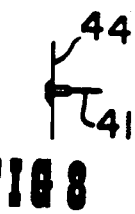
FIG 8

"PEEPER" PERFORMANCE HAND HELD NEBULIZER ATTACHMENT WITH ADJUSTABILITY OF EXPIRATORY PRESSURES AND EXPIRATORY RESTRICTION

BACKGROUND OF THE INVENTION

This invention relates to the delivery of aerosolized medications for inhalation, specifically with the addition of adjustable and inadvertant positive expiratory pressures.

BACKGROUND DESCRIPTION OF PRIOR ART

The prior art in nebulization of medications for hospitals, home care, and paramedical care of inhalation therapy, consisted of an open system in which the patient draws in medication and ambient air through a nebulizer, flex tube, tee piece and mouthpiece. This is a pneumatic device powered by a connecting tube to an air or an oxygen gas source.

These nebulizer units are commonly disposable and intended for single patient use only. They are designed to break up liquid medication into micron size particles which is entrained into the stream of gas flow. This provides an aerosol for respiratory therapy in the treatment of chronic and/or acute pulmonary disorders or injuries. The aerosol provided by the nebulizer is designed to give a sufficient quantity and proper formation of liquid particles when administered properly in conjunction with effective patient inhalation effort. The ideal micron size has a range of 0.2 to 3.0 microns for proper deposition in the pulmonary system. If the particles are too large they may be deposited in the upper respiratory tract and if these aerosolized particles are too fine they will be carried out during exhalation. The results are a significant loss of medication or aerosolized particles exiting the nebulizer therefore causing loss of medication to the patient. These prior art nebulizer units make it difficult for the patient to control the rate of delivery of nebulized liquid due to insufficient inspiratory effort, typical of pulmonary disorders. Deposition of aerosolized medication into the pulmonary system and the effectiveness of the medication relies on the rate and depth of the patients respiratory effort. All of these commercially available nebulizers on the market today (or commonly called "hand-held nebulizers"), all have the same problem of losing a portion of the liquid medication after nebulization through the process of exhalation and continuous gas flow through an open system. They also have no means to assist the delivery of medication deep into the lungs without the addition of specific and costly equipment.

Previous patents such as U.S. Pat. No. 3,762,409, Lester (1973) and U.S. Pat. No. 3,512,341, Lester (1985) disclose the mechanical means of aerosolizing liquid medications, however, they do not provide patient controlled means of delivery of medication to the patient and does not contain adjustable control over exhaled pressures or a delivery of medication to the patient without waste.

Another drawback with standard nebulizers is that they do not direct the entire volume of liquid medication to the patient with present prior art delivery systems. Medication is continually flowing in an aerosol form out of the nebulizer and into the prior art commonly used tee connector. This directs the aerosol to the patient through a mouthpiece and also directs the medication out of the distal end of the tee connector resulting in a constant loss of medication via the pneumatic operation of the nebulizer and through the patients own exhalation force. Most nebulizer kits come with a six inch piece of flexible wide-bore tubing, which is most commonly placed in the distal end of the tee connector for the purpose of directing this continuous flow of aerosolized medication away from the patients face.

The present invention is a nebulizer assembly that utilizes a one-way valve within a rigid tubular connector to form a semi-closed delivery system, thus directing all aerosolized medication to the patient and virtually eliminating aerosol waste through its distal end out into the atmosphere.

Respiratory Practitioners have long recognized the need for a patient-operated inhalation device that provides each individual patient, control over their own tidal volume needs along with the benefit of deeper aerosol deposition through positive expiratory pressures also known as a "pursed-lip breathing technique" to improve alveolar oxygenation, relieve trapping of carbon dioxide and improve the delivery and efficacy of bronchodilators, the most commonly used medication for pulmonary disorders.

Prior U.S. Pat. No. 4,253,468, Lehmbeck (1981), refers to a one-way valve in the tee connector. This design does not allow for a semi-closed system with any option of controlling expiratory pressures. The patient can not control aerosol delivery or prevent aersolized medication waste through the open end of this delivery system. Another drawback to the last named patent is that the patient must remove the nebulizer from their mouth in order to exhale because of the one-way valve configuration. The one-way valve is arranged between the nebulizer and the patient's mouth to permit the passage of air only in the direction from the ambient towards the inhalation inlet with no passageway for exhalation. This configuration also increases waste of medication to the atmosphere.

Prior U.S. Pat. No. 4,446,863, Ruben (1984), refers to a nebulizer attachment of an incentive spirometer at the distal end of the tee. This patent is an attempt to combine an exerciser and an aerosolized medication delivery system into one unit, however, adjustments can be made to monitor inspiratory flow only. As with the other background and prior arts, it does not give patients the option of patient control over their expiratory pressures or prevent waste of aerosolized medications due to its open system. The last named patent utilizes an incentive spirometer which is generally administered to patients as a frequent exerciser, where as the nebulizer is for the delivery of aerosolized medications and must be restricted in frequency of use because of the medications. The incentive spirometer and the nebulizer are designed to do two different and separate functions, thus making the prior art device needlessly expensive and bulky for the respiratory patient.

OBJECTS AND ADVANTAGES

The present invention provides an attachment for use with a standard hand-held nebulizer, serving as a patient controllable, adjustable device designed to provide positive expiratory pressures, provide for a semi-closed aerosol reservoir delivery system, and prevent waste of medication to the atmosphere.

It is a primary object of the present invention to provide a specialized delivery system in conjunction with a standard hand-held nebulizer that can easily provide a variety of options and lung volume maneuvers to the pulmonary patient which is relatively inexpensive and simple to manufacture.

It is a further object to provide a breathing apparatus to imitate (commonly and frequently unconscious) pursed-lip breathing. This is a lung mechanics maneuver to keep the lungs partially expanded during exhalation. It is a self-imposed form of exhalation retard most commonly used by asthmatics to help in alleviating the air trapping or the trapping of carbon dioxide within the alveoli.

Still another object is to provide a breathing device maneuver in which air trapping is relieved. Air trapping is the result of the patient not being able to completely eliminate or exhale all of the air from his lungs. This is common in most respiratory diseases, thus alveolar gas delivery is decreased on inspiration because expiratory flows are impeded.

Another important object is to provide another breathing device maneuver called expiratory retard. Expiratory retard is the maintenance of expiratory flow for a longer period of time. The function of the expiratory retard in severe obstructive lung disease is to improve expiratory flow by manipulating the point where equal pressures exists. An "equal pressure point" is where the ambient room pressure equals or matches the intrathoracic pressures of the lungs.

Yet another object is to provide P.E.E.P. (Positive end-expiratory pressure) which is quantitative and controlled maneuver produced for the patient to maintain above atmospheric pressure at the end of expiration. Positive end-expiratory pressure is a maneuver used for restricted lung disorders in which only prior art, costly, mechanical devices were available. Positive end-expiratory pressures are used in the present invention, a hand-held device which assists in the treatment of restrictive as well as chronic obstructive lung disease.

It is another object to provide Inadvertant P.E.E.P. (positive end-expiratory pressure) which is controllable and can easily be maneuvered by the patient. With the present invention the patient can fluctuate the amount of positive pressure upon exhalation by simply flexing the hand-held nebulizer assembly, thus opening or closing the exhalation holes positioned within the housing of the flexible tubing. Costly and mechanical traditional prior art P.E.E.P. is not readily controlled and accessible by the patient. This invention provides the full range of expiratory pressures for the patient to control for their benefit without restriction of pre-set controls or bulky equipment. Therefore, inadvertant P.E.E.P. is the opposite of current P.E.E.P. in regards to adjustability and control.

It is a further object to provide a system whereas the aerosolized medication is not wasted into the ambient room air, but instead delivered directly to the patient. Thus, wasted, aerosolized medication is controllable and minimal. The present invention provides for a semi-closed system whereas the medications are entirely directed to the patient's respiratory system for the desired and intended maximum beneficial effect possible.

Still another object is to provide a rigid tubular conduit, housing an one-way valve assembly at its most distal position to the patient. This present invention unit will attach to any standard hand-held nebulizer outlet neck creating a horizontal pathway to direct the flow of aerosolized medications to the patient only and block the patients exhaled pressures. The present inventions multi-purpose tubular conduit may also incorporate an indention used for a finger rest to provide better control of the flexing maneuvers inherent with the present invention.

Another important object is to provide a flexible, corrugated, plastic or polyvinyl (or other similar material) multi-ribbed tube, which can be angled and maneuvered into a position of 0 degrees to a maximum of 90 degrees. When reduced to practice the length should be approximately 4 inches (10 cm) and the diameter 13/16 of an inch (22 mm). The present invention's flexible tube provides 1 or more holes (disclosed in the specifications) to provide for an exhalation route. The control of exhalation pressures including P.E.E.P. (positive end-expiratory pressures as mentioned above) is accomplished when the patient bends the flex tubing with a slight tilting of the nebulizer and assembly.

It is another object to provide through the exhalation route of the flexible tubing, an arrangement of one or more holes, or exhalation vents. These exhalation vents are to be cut out or punched out in shapes such as lozenge, oval, syncline, rectangle or any combination there of, but not restricted to. The present inventions exhalation vents are placed to give optimum function by opening and closing to change exhalation restrictions in a range of 0 to 80 cm/H20 or 0 to 109 mm/Hg with minimal manipulation of the present invention assembly by the operator or patient.

It is a further object to provide a rigid "O" shaped or a large oval shaped mouthpiece incorporated at the patient end of the flexible wide-bore tubing. This round shape is to provide the patient more comfort in receiving aerosolized medications. It is observed that patients in respiratory distress are unconsciously air gulping and are unable to close their mouth around the conventional flat mouthpiece. This "O" shaped mouthpiece has a universal size of 22 mm O.D. and 15 mm I.D. to conveniently mate with a conventional mouthpiece, mask, or Other types of airway devices. Therefore, this invention provides a range of options that can be incorporated for the patients benefit and comfort.

It is another object to provide in the present invention's assembly members an oxygen supply tubing with a threaded outlet coupling for easy attachment to any oxygen or compressed air flowmeter or regulator supply device without the addition of specific nipple adaptors, and may also be used with a nipple attachment to a flowmeter. At the other end of the oxygen supply tubing, a standard push-on nipple coupling is provided for easy attachment to the nebulizer bowl.

In summation the objects and intent of the present invention is to provide a simple, inexpensive, convenient, disposable and effective means of delivering aerosolized medications to the patient with the option to control the exhalation pressures and restrictions and to provide the patient with their own control over the maneuvers of the present invention and to provide maximal deposition of the aerosolized medications to the patients pulmonary tract, to ensure that all the medications are delivered and are not eliminated through exhalation or weak and improper inspiration, and to provide a system for patients to increase alveolar gas exchange, effective peak expiratory flows, and arterial oxygen saturations, by performing simple expiratory pressure maneuvers. Other objects and advantages will become apparent when taken in consideration with the following drawings and specifications.

BRIEF DESCRIPTION OF THE DRAWINGS

FIG. 3-A is a side view of a flexible tube section in a closed position.

FIG. 3-B is a side view of a flexible tube section in an open position.

FIG. 3-C is an exploded side view of the device.

FIG. 3-D is a sectional view showing V shaped exit vents.

FIG. 3-E is a sectional view showing oval shaped exit vents.

FIG. 3-F is a sectional view showing rectangular shaped exit vents.

FIG. 4-A is a perspective view of the tee sections.

FIG. 4-B is a section taken at A—A of FIG. 4A.

FIG. 4-C is a section taken at B—B of FIG. 4A.

FIG. 5 is a oval shaped mouthpiece.

FIG. 6 is a section taken at C—C of FIG. 5.

FIG. 7 is a section taken at D—D of FIG. 4C.

FIG. 8 is a side view of FIG. 7.

DETAILED DESCRIPTION OF THE DRAWINGS

Figure 1:
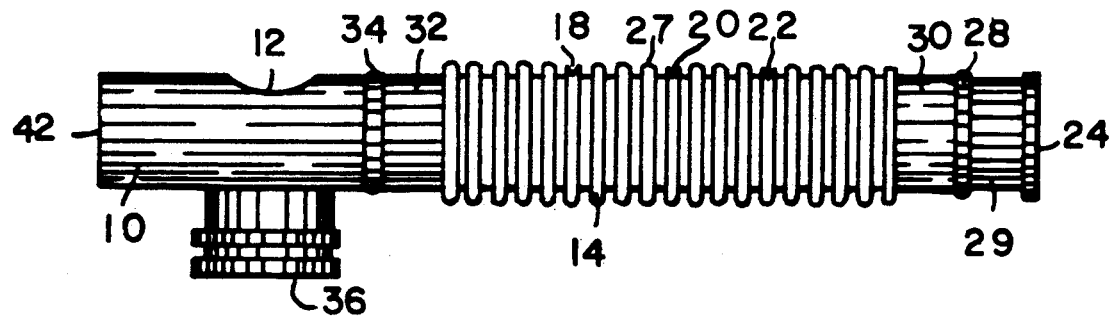
FIG. 1 is a side view of the device attached to a prior art hand-held nebulizer.
Figure 2:
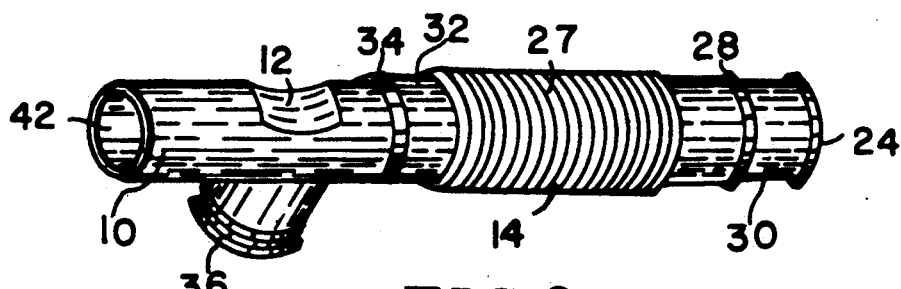
FIG. 2 is a perspective view.

Referring to FIG. 1, there is shown a disposable aerosol inhalation assembly for use in converting liquid medication into an aerosol form for delivery by inhalation. The hand-held nebulizer 50 is of conventional construction and accordingly will not be described herein in detail, but reference is made to U.S. Pat. Nos. 3,762,409 and 4,512,341. The nebulizer 50 is mated within the lumen 48 of a T shaped rigid cylindrical conduit tube 10 here in referred to as a rigid tubular conduit 10. The lumen 36 is approximately 15 mm in diameter for standard adaptability to most medical nebulizers. The aerosolized medication generated from the nebulizer 50 when connected to an oxygen or air source at an appropriate flow, flows directly into the interior chamber of the rigid tubular conduit 10 from the nebulizers outlet 51. Referring to FIG. 4-C, the interior of the rigid tubular conduit 10 contains one exit port 48 thereby continuing flow of aerosolized medication directly towards the patient. The distal end 42 of the horizontal limb of the rigid tubular conduit 10 houses a rigid framework 46 and an annular lip 47 to support and contain a thin rubber, latex, or similar flexible material membrane known as an one-way valve 44 as illustrated in FIGS. 7 and 8. The valve membrane 44 seats against the annular lip 47 and framework 46 to form a tight seal and closure entrapping flow of aerosolized solution from the nebulizing system against exiting into the atmosphere and thereby preventing waste of inhalation solution as with conventional nebulizing systems. FIG. 4-C illustrates with arrows, the motion of the diaphram having a dual action by preventing loss of aerosol by occluding the port 42 and providing a port of entry for entraining air from the atmosphere only when patient inhales according to this invention. FIG. 4-A illustrates the open, opposing end 48 of the rigid tubular conduit 10 providing passage of aersolized medication to the patient. Referring to FIG. 2 and 3-C, attached to this open end 48 of the rigid tubular conduit 10 is a flexible, multi-ribbed extension tubing 27 of polyvinyl substance of similar material of approximately 22 mm inside diameter and approximately 4 inches long (length may vary permitting for optimal manipulation). Each end of the flexible tubing 27 is identical containing one joint ring 28, 34 and inner, wide flat rings 30, 32 for ease of receiving rigid conduit connections by friction method. Referring to FIG. 3-D, 3-E and 3-F there is shown three different sized openings 21, 23, and 25 in the outer ring 14 positioned of equal distance apart and intended for the proximal side of the flexible tubing 27 according to this invention. Illustrated in FIGS. 3-A and 3-B flexible tubing 27 is manipulated in either a downward or upward motion in variable degrees thus applying a method of increasing or decreasing the orifice of each exhalation vent 18, 20, and 22 according to the present invention. Attached by friction method at the patient end of the flexible tubing 27, in FIG. 3-C, is a rigid cylindrical mouthpiece 29 according to the present invention for the purpose of providing a larger passageway 24 for the patient (not shown) having difficulty breathing to receive air and medication without compromising comfort. The "0" mouthpiece 29 is of a universal inside diameter of 15 mm to accept the attaching end of any standard mouthpiece to provide optimal comfort to the patient. 12 is a recessed area creating a finger hold.

FIG. 3-C illustrates the assembly of the invention. When the patient inhales through the "0" mouthpiece 29, the flexible tubing 27, and the rigid tubular conduit 10, the membrane 44 of the one-way valve 41 opens to permit entraining of room air to travel along the passageway with the continuing flow of nebulized gas and liquid directly to the patients lungs. At termination of inhalation and/or upon exhalation, the membrane 44 of the one-way valve 41 closes preventing escape of nebulized gas and liquid and the patients exhaled breath. Upon exhalation, the patient has the option of exhaling passively through the exhalation vents 18, 20, and 22 by positioning the flexible tubing 27 downward to increase the orifice as in FIG. 3-B. The resistance to exhalation is measurable to 0 cm H20 with exhalation vents 18, 20, and 22 opened to maximum limit. Upon exhalation, the patient has the option of creating a variety of exhalation vents 18, 20, and 22 by positioning the flexible tubing 27 upwards as in FIG. 3-A. The exhalation resistance is measurable from 1 cm to 100 cm H20. During exhalation the patient can manipulate the flexible tubing 27 to adjust the exhalation vents 18, 20, and 22 to create a variety of lung maneuvers such as positive end-expiratory pressure, expiratory retard, inadvertant positive expiratory pressures, pursed-lip breathing and inspiratory hold. These techniques keep the lungs open longer to relieve air-trapping, eliminate carbon dioxide build-up and increase optimal medication deposition.

SUMMARY, RAMIFICATIONS AND SCOPE

Accordingly, the reader will see the advantages to this invention by examining the improvements incorporated in this invention's embodiment.

Accordingly, to this invention, there is provided for use with a standard hand-held nebulizer an attachment serving as a device for providing a patient or respiratory practitioner with control of exhalation restrictions and/or positive expiratory pressures which is self contained, easy to operate, universal in size, inexpensive to manufacture, and beneficial to the patient in the treatment of respiratory disease or injury.

Currently, in todays market, no device (known to the inventor) exists with the capabilities of providing a self contained, semi-closed system in a hand-held nebulizer assembly with the option of delivering an exhalation restriction providing positive expiratory pressure with means to be maneuvered and controlled by the patient or respiratory practitioner as deemed.

Positive expiratory pressure is useful in the treatment of respiratory patients because it provides an expiratory airway pressure maneuver in which the airway pressure is maintained above atmospheric pressure at the end of the expiration. Respiratory therapy is concerned with manipulation of airway pressures to provide improved ventilatory mechanics and physiologic gas exchange.

In a preferred embodiment of the present invention, the aforementioned rigid tubular conduit, housing an one-way valve is a modification of a standard tee connector. This modification prevents the free flowing aerosolized gas and medications from escaping through the outlet to the atmosphere.

The aforementioned wide-bore flexible tubing with the predetermined exhalation vents of specific shape and size, fully incorporates and utilizes this device for maximum benefit to the patient.

Although the description above contains specifics, these should not be construed as limiting the scope of the present invention but as merely providing illustrations of some of the presently preferred embodiments. For example, the exhalation vents can have other shapes such as: circular, oval, square, rectangle, trapezoid, hexagon, and any shape that would be of use in this preferred embodiment.

In addition, this nebulizer attachment is not limited to standard treatment protocol using a mouthpiece for respiratory patients, i.e., chronic obstructive pulmonary disease, acute or chronic restrictive pulmonary disease, but may be used in conjunction with respiratory failure, code blue (cardio-pulmonary resuscitation) situations, pediatrics, neonates, ventilator care, pulmonary function testing and home care. Because, with the present invention, the preferred embodiment utilizes a universal size for the proper fit of other types of mouthpieces, masks, flexible tubing and resuscitation devices, therefore options and delivery is universal.

Thus, the scope of the invention should be determined by the appended claims and their legal equivalents, rather than by the examples given.

What I claim and wish to secure by letters patent is:

1. An attachment device for use with a hand-held aerosol generating nebulizer, said attachment device comprising a tee section, a flexible hose section and a mouthpiece, said tee section having a first leg, a second leg and a common leg, said common leg including means for connection with a hand-held aerosol generating nebulizer, said first leg including an internal valve means, said second leg including means for connecting said second leg to said flexible hose section, said flexible hose section including means for connecting said flexible hose section to said mouthpiece, said flexible hose section having at least one exit vent located in the wall of the material forming said flexible hose substantially centrally intermediate the ends of said flexible hose, said exit vent having an open position and a closed position, said vent is moved from said closed position to said open position in response to bending of said flexible hose section, and said vent returns to a position approximately midway between said open position and said closed position upon a return of said flexible hose to a straight condition.

2. The device of claim 1 in which said internal valve means comprises a one-way valve having an open position and a closed position, said one-way valve being biased to said closed position.

3. The device of claim 2 in which said one-way valve comprises a flexible diaphragm which upon inhalation, said diaphragm is drawn away from a rigid framework, whereby permitting entrainment of atmospheric air respondent only upon patient volume demand.

4. The device of claim 3 in which said flexible diaphragm is made of rubber.

5. The device of claim 3 in which said flexible diaphragm is made of latex.

6. The device of claim 1 in which said flexible hose section has multiple ribs, said multiple ribs containing at least one exit vent.

7. The devices of claim 1 in which said means for connection with a head-held aerosol generating nebulizer, said means for connecting said second leg to said flexible hose section, and said means for connecting said flexible hose section said mouthpiece are a friction fit.

8. The device of claim 1 in which said exit vents are Vee shaped.

9. The device of claim 1 in which said exit vents are oval shaped.

10. The device of claim 1 in which said exit vents are rectangularly shaped.

11. The device of claim 1 in which said mouthpiece is oval shaped.

12. The device of claim 1 in which said tee section has a finger support.

13. The device of claim 12 in which said finger support is a substantially inwardly curving section located opposite said common leg of said tee section.

14. The device of claim 1 in which said tee section is a substantially rigid tubular conduit.

* * * * *